(12) United States Patent
Hardert et al.

(10) Patent No.: US 8,025,495 B2
(45) Date of Patent: Sep. 27, 2011

(54) APPARATUS AND METHOD FOR MAKING A SPIDER OCCLUSION DEVICE

(75) Inventors: Michael W. Hardert, Bloomington, IN (US); Arman H. Valaie, Bloomington, IN (US); Kevin L. Delaney, Bloomington, IN (US); Christopher L. Hruska, Bloomington, IN (US); Sarah E. Waite, Cory, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1065 days.

(21) Appl. No.: 11/845,455

(22) Filed: Aug. 27, 2007

(65) Prior Publication Data

US 2009/0061136 A1    Mar. 5, 2009

(51) Int. Cl.
*B29C 70/00* (2006.01)
*B28B 7/00* (2006.01)

(52) U.S. Cl. .............. 425/110; 425/174.4; 425/470; 264/279.1

(58) Field of Classification Search .................. 425/110, 425/174.4, 470; 264/255, 263, 279.1
See application file for complete search history.

(56) References Cited

U.S. PATENT DOCUMENTS

| | | | |
|---|---|---|---|
| 3,012,882 A | 12/1961 | Muldawer et al. | |
| 3,174,851 A | 3/1965 | Buehler et al. | |
| 3,772,137 A | 11/1973 | Tolliver | |
| 3,953,566 A | 4/1976 | Gore | |
| 4,662,885 A | 5/1987 | DiPisa, Jr. | |
| 4,665,906 A | 5/1987 | Jervis | |
| 4,675,361 A | 6/1987 | Ward, Jr. | |
| 4,861,830 A | 8/1989 | Ward, Jr. | |
| 4,917,089 A | 4/1990 | Sideris | |
| 5,017,664 A | 5/1991 | Grasel et al. | |
| 5,024,671 A | 6/1991 | Tu et al. | |
| 5,108,420 A | 4/1992 | Marks | |
| 5,334,217 A | 8/1994 | Das | |
| 5,417,708 A | 5/1995 | Hall et al. | |
| 5,451,235 A | 9/1995 | Lock et al. | |
| 5,589,563 A | 12/1996 | Ward et al. | |
| 5,595,571 A | 1/1997 | Jaffe et al. | |
| 5,643,317 A | 7/1997 | Pavcnik et al. | |
| 5,651,174 A * | 7/1997 | Schwartz et al. | ............ 29/527.2 |

(Continued)

OTHER PUBLICATIONS

Dušan Pavčnik et al., Monodisk: Device for Percutaneous Transcatheter Closure of Cardiac Septal Defects, CardioVascular and Interventional Radiology, vol. 16, pp. 308-312, 1993.

(Continued)

*Primary Examiner* — Maria Veronica Ewald
(74) *Attorney, Agent, or Firm* — Brinks Hofer Gilson & Lione

(57) ABSTRACT

An apparatus and method for making an occlusion device for occluding a body vessel. The apparatus and method include providing a frame and a mandrel. The frame has a hub extending along a longitudinal axis from a proximal end to a distal end. A plurality of arcuate legs are attached to the hub and extend distally. The arcuate legs are flexible and have inner surfaces defining an inner profile in an unconstrained state. The mandrel has an outer surface corresponding to the inner profile of the occlusion device. A base layer of a biocompatible material is disposed on the outer surface of the mandrel. The frame is placed on the outer surface with the base layer between the frame and the mandrel. The frame is attached to the base layer such that the biocompatible material forms a membrane extending along and between the arcuate legs.

8 Claims, 6 Drawing Sheets

U.S. PATENT DOCUMENTS

| | | | |
|---|---|---|---|
| 5,669,933 | A | 9/1997 | Simon et al. |
| 5,683,411 | A | 11/1997 | Kavteladze et al. |
| 5,690,642 | A | 11/1997 | Osborne et al. |
| 5,720,777 | A | 2/1998 | Jaffe et al. |
| 5,725,534 | A | 3/1998 | Rasmussen |
| 5,733,337 | A | 3/1998 | Carr, Jr. et al. |
| 5,769,796 | A | 6/1998 | Palermo et al. |
| 5,797,953 | A | 8/1998 | Tekulve |
| 5,797,960 | A | 8/1998 | Stevens et al. |
| 5,814,061 | A | 9/1998 | Osborne et al. |
| 5,843,180 | A | 12/1998 | Jaffe et al. |
| 5,843,181 | A | 12/1998 | Jaffe et al. |
| 5,846,247 | A | 12/1998 | Unsworth et al. |
| 5,846,261 | A | 12/1998 | Kotula et al. |
| 5,861,003 | A | 1/1999 | Latson et al. |
| 5,944,738 | A | 8/1999 | Amplatz et al. |
| 5,947,997 | A | 9/1999 | Pavcnik et al. |
| 5,960,642 | A | 10/1999 | Kim et al. |
| 5,980,799 | A | 11/1999 | Martakos et al. |
| 5,993,844 | A | 11/1999 | Abraham et al. |
| 6,063,113 | A | 5/2000 | Kavteladze et al. |
| 6,117,157 | A | 9/2000 | Tekulve |
| 6,206,907 | B1 | 3/2001 | Marino et al. |
| 6,206,931 | B1 | 3/2001 | Cook et al. |
| 6,214,029 | B1 | 4/2001 | Thill et al. |
| 6,251,143 | B1 | 6/2001 | Schwartz et al. |
| 6,346,074 | B1 | 2/2002 | Roth |
| 6,355,052 | B1 | 3/2002 | Neuss et al. |
| 6,358,228 | B1 | 3/2002 | Tubman et al. |
| 6,358,284 | B1 | 3/2002 | Fearnot et al. |
| 6,368,338 | B1 | 4/2002 | Kónya et al. |
| 6,371,961 | B1 | 4/2002 | Osborne et al. |
| 6,451,052 | B1 | 9/2002 | Burmeister et al. |
| 6,458,137 | B1 | 10/2002 | Klint |
| 6,547,815 | B2 | 4/2003 | Myers |
| 6,554,849 | B1 | 4/2003 | Jones et al. |
| 6,572,650 | B1 | 6/2003 | Abraham et al. |
| 6,616,680 | B1 | 9/2003 | Thielen |
| 6,656,206 | B2 | 12/2003 | Corcoran et al. |
| 6,673,100 | B2 | 1/2004 | Diaz et al. |
| 6,752,826 | B2 | 6/2004 | Holloway et al. |
| 6,790,218 | B2 | 9/2004 | Jayaraman |
| 6,939,377 | B2 | 9/2005 | Jayaramann et al. |
| 6,994,092 | B2 | 2/2006 | van der Burg et al. |
| 6,994,717 | B2 | 2/2006 | Kónya et al. |
| 7,101,395 | B2 | 9/2006 | Tremulis et al. |
| 2001/0025187 | A1 | 9/2001 | Okada |
| 2001/0039450 | A1 | 11/2001 | Pavcnik et al. |
| 2002/0029051 | A1 | 3/2002 | Callister et al. |
| 2002/0038151 | A1 | 3/2002 | Plouhar et al. |
| 2002/0111647 | A1 | 8/2002 | Khairkhahan et al. |
| 2002/0187288 | A1 | 12/2002 | Lim et al. |
| 2002/0198563 | A1 | 12/2002 | Gainor et al. |
| 2003/0028213 | A1 | 2/2003 | Thill et al. |
| 2003/0051735 | A1 | 3/2003 | Pavcnik et al. |
| 2003/0057156 | A1 | 3/2003 | Peterson et al. |
| 2003/0093108 | A1 | 5/2003 | Avellanet et al. |
| 2003/0139819 | A1 | 7/2003 | Beer et al. |
| 2003/0144694 | A1 | 7/2003 | Chanduszuko et al. |
| 2003/0149471 | A1 | 8/2003 | Brianna et al. |
| 2003/0191495 | A1 | 10/2003 | Ryan et al. |
| 2003/0206860 | A1 | 11/2003 | Bleyer et al. |
| 2004/0073242 | A1 | 4/2004 | Chanduszko |
| 2004/0087999 | A1 | 5/2004 | Bosma et al. |
| 2004/0093017 | A1 | 5/2004 | Chanduszko |
| 2004/0098030 | A1 | 5/2004 | Makower et al. |
| 2004/0098042 | A1 | 5/2004 | Devellian et al. |
| 2004/0143277 | A1 | 7/2004 | Marino et al. |
| 2004/0143293 | A1 | 7/2004 | Marino et al. |
| 2004/0166169 | A1 | 8/2004 | Malaviya et al. |
| 2004/0176799 | A1 | 9/2004 | Chanduszko et al. |
| 2004/0199242 | A1* | 10/2004 | Hong et al. ............ 623/1.16 |
| 2004/0213756 | A1 | 10/2004 | Michal et al. |
| 2004/0220610 | A1 | 11/2004 | Kreidler et al. |
| 2004/0225324 | A1 | 11/2004 | Marino et al. |
| 2005/0043759 | A1 | 2/2005 | Chanduszko |
| 2005/0070794 | A1 | 3/2005 | Deal et al. |
| 2005/0070821 | A1 | 3/2005 | Deal et al. |
| 2005/0085843 | A1 | 4/2005 | Opolski et al. |
| 2005/0125050 | A1 | 6/2005 | Carter et al. |
| 2005/0154252 | A1 | 7/2005 | Sharkey et al. |
| 2005/0203568 | A1 | 9/2005 | Burg et al. |
| 2005/0228434 | A1 | 10/2005 | Amplatz et al. |
| 2005/0249772 | A1 | 11/2005 | Malaviya et al. |
| 2005/0256532 | A1 | 11/2005 | Nayak et al. |
| 2005/0267524 | A1 | 12/2005 | Chanduszko |
| 2005/0273124 | A1 | 12/2005 | Chanduszko |
| 2005/0273135 | A1 | 12/2005 | Chanduszko et al. |
| 2005/0288706 | A1 | 12/2005 | Widomski et al. |
| 2005/0288786 | A1 | 12/2005 | Chanduszko |
| 2006/0009800 | A1 | 1/2006 | Christianson et al. |
| 2006/0030881 | A1 | 2/2006 | Sharkey et al. |
| 2006/0052816 | A1 | 3/2006 | Bates et al. |
| 2006/0106420 | A1 | 5/2006 | Dolan et al. |
| 2006/0201996 | A1 | 9/2006 | Hodde |
| 2006/0210603 | A1 | 9/2006 | Williams et al. |
| 2006/0216326 | A1 | 9/2006 | Pacetti |
| 2006/0235463 | A1 | 10/2006 | Freudenthal et al. |
| 2006/0271030 | A1 | 11/2006 | Francis et al. |
| 2007/0179527 | A1 | 8/2007 | Eskuri et al. |

OTHER PUBLICATIONS

Christian Jux, M.D. et al., A New Biological Matrix for Septal Occlusion, Journal of Interventional Cardiology, vol. 16, No. 2, pp. 149-152, 2003.

Christian Jux, M.D. et al., Interventional Atrial Septal Defect Closure Using a Totally Bioresorbable Occluder Matrix, Journal of the American College of Cardiology, vol. 48, No. 1, pp. 161-169, Jul. 2006.

Amplatz Vacular Obstruction Device, Cook Medical Inc., 4pp., 2005.

* cited by examiner

APPARATUS AND METHOD FOR MAKING A SPIDER OCCLUSION DEVICE

BACKGROUND

1. Field of the Invention

The present invention generally relates to vascular occlusion devices. More specifically, the invention relates to an apparatus and method of making a spider shaped device with an occlusive barrier.

2. Description of Related Art

A number of different devices may be used to occlude a body cavity, for example, a blood vessel. When it is desirable to quickly occlude a blood vessel, an inflatable balloon may be used. However, balloon's have the disadvantage of being temporary. Another example of an occlusion device includes embolization coils. Embolization coils are permanent and promote blood clots or tissue growth over a period of time, thereby occluding the body cavity. In conjunction with the embolization coil, a spider shaped vascular obstruction device may be used to prevent dislodgment of the embolization coil while the blood clots or the tissue grows. A problem with this arrangement is that blood may continue to flow past the coil and spider device and through the body cavity until it finally occludes. It may take a significant period of time for sufficient tissue to grow to fully occlude the body cavity. This leaves a patient open to a risk of injury from the condition which requires the body cavity to be occluded. Also, since this arrangement is more complex since it requires the delivery of two separate devices to the vasculature.

In view of the above, it is apparent that there exists a need for an improved vascular occlusion device capable of occluding a body vessel quickly.

SUMMARY

In satisfying the above need, as well as overcoming the enumerated drawbacks and other limitations of the related art, the present invention provides an apparatus for making a vascular occlusion device. The apparatus has a frame a frame including a hub extending along a longitudinal axis from a proximal end to a distal end, a plurality of arcuate legs being attached to the hub and extending distally to a distal leg portion, the arcuate legs being flexible and having inner surfaces defining an inner profile extending radially away from the longitudinal axis in an unconstrained state. The apparatus also includes a mandrel having an outer surface corresponding to the inner profile of the frame, and a source of a liquid biocompatible material. The liquid biocompatible material is releasably disposed from the source onto the outer surface of the mandrel and is allowed to dry into a solid biocompatible base layer. The inner profile of the arcuate legs of the frame are disposed over the outer surface of the mandrel onto the base layer. The arcuate legs are attached to the base layer by, for example, disposing additional liquid biocompatible material over the frame to encapsulate a portion of each of the arcuate legs and form a membrane extending along and between each of the arcuate legs.

In a first embodiment, the frame is attached to the biocompatible material by disposing a second layer of the biocompatible material over the frame such that the second layer attaches to the base layer and substantially encapsulates the frame. In a second embodiment, a plurality of second layers of the biocompatible material are disposed over a portion of each of the plurality of arcuate legs to attach the base layer to the arcuate legs. In a third embodiment, a portion of each of the arcuate legs are stitched to the biocompatible material.

In some instances, it may be desirable to provide a plurality of small holes in the membrane. The small holes may be provided by means of, for example, laser cutting.

Some examples of the biocompatible material include, but are not limited to, nylon, rayon, silicone, polyester, polytetrafluroethylene, urethane, biocompatible polyurethanes, and mixtures thereof.

In addition, the frame may be made of a shape memory material. One example of the shape memory material includes, but is not limited to, alloys of nickel-titanium.

The present invention also includes a method of making an occlusion device for occluding a body vessel. The method includes supplying a frame similar to that described above. The method also includes providing a mandrel having an outer surface corresponding to the inner profile of the occlusion device and disposing a base layer of a biocompatible material on the outer surface of the mandrel. In addition, the method includes placing the frame on the biocompatible material on the mandrel such that at least part of the inner surfaces of the arcuate legs contact the biocompatible material and attaching the frame to the biocompatible material such that the biocompatible material forms a membrane extending along and between each of the plurality of legs.

In some examples, the base layer is disposed on the outer surface of the mandrel by dipping the outer surface into a liquid biocompatible material which is then dried on the mandrel. However, in other examples it may also be possible to dispose the base layer onto the mandrel by other means including, but not limited to, by spraying.

Further objects, features and advantages of this invention will become readily apparent to persons skilled in the art after a review of the following description, with reference to the drawings and claims that are appended to and form a part of this specification.

DETAILED DESCRIPTION

Figure 1:
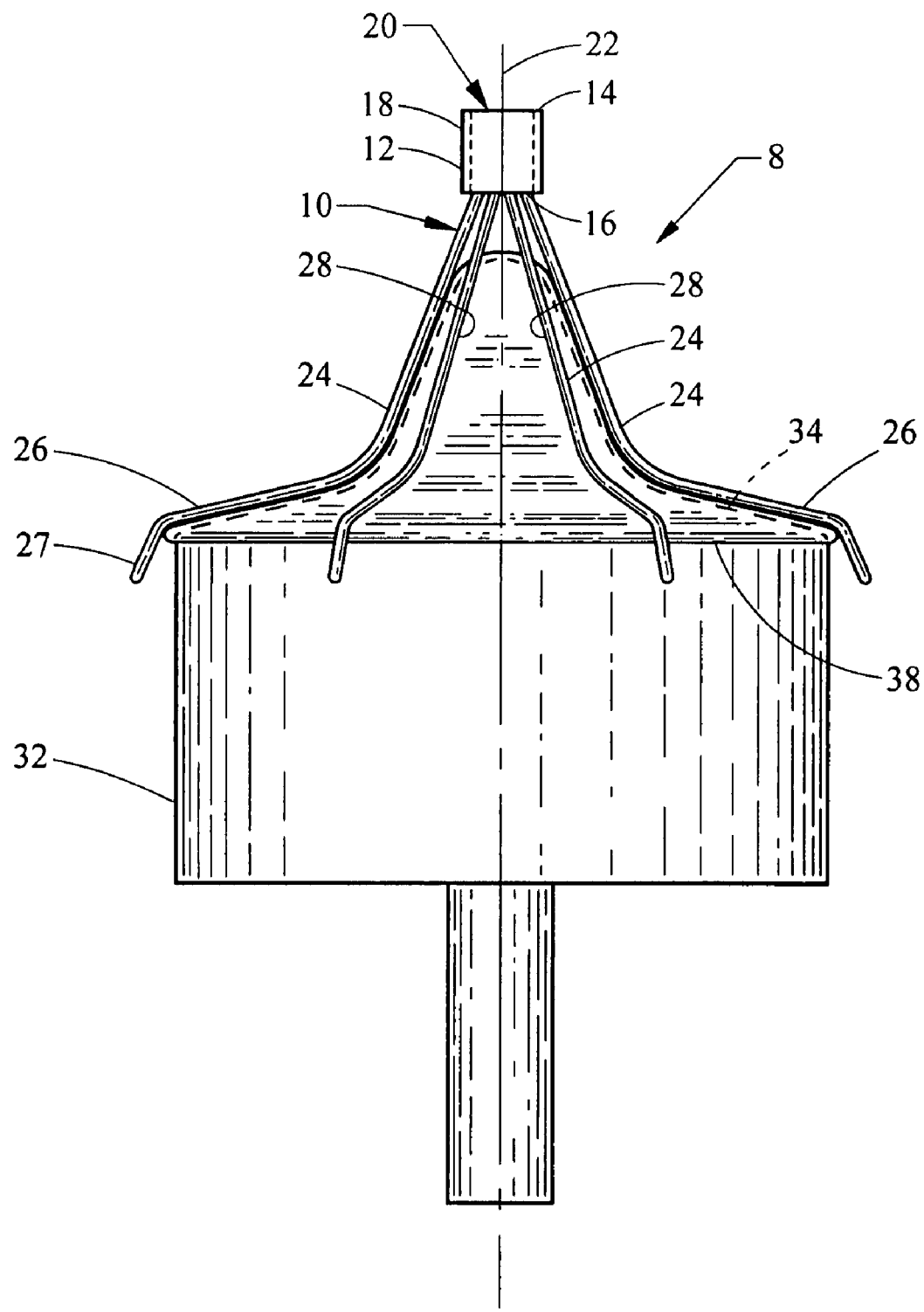
FIG. 1 is a side view of an apparatus for making an occlusion device according to the present invention.
Figure 2:
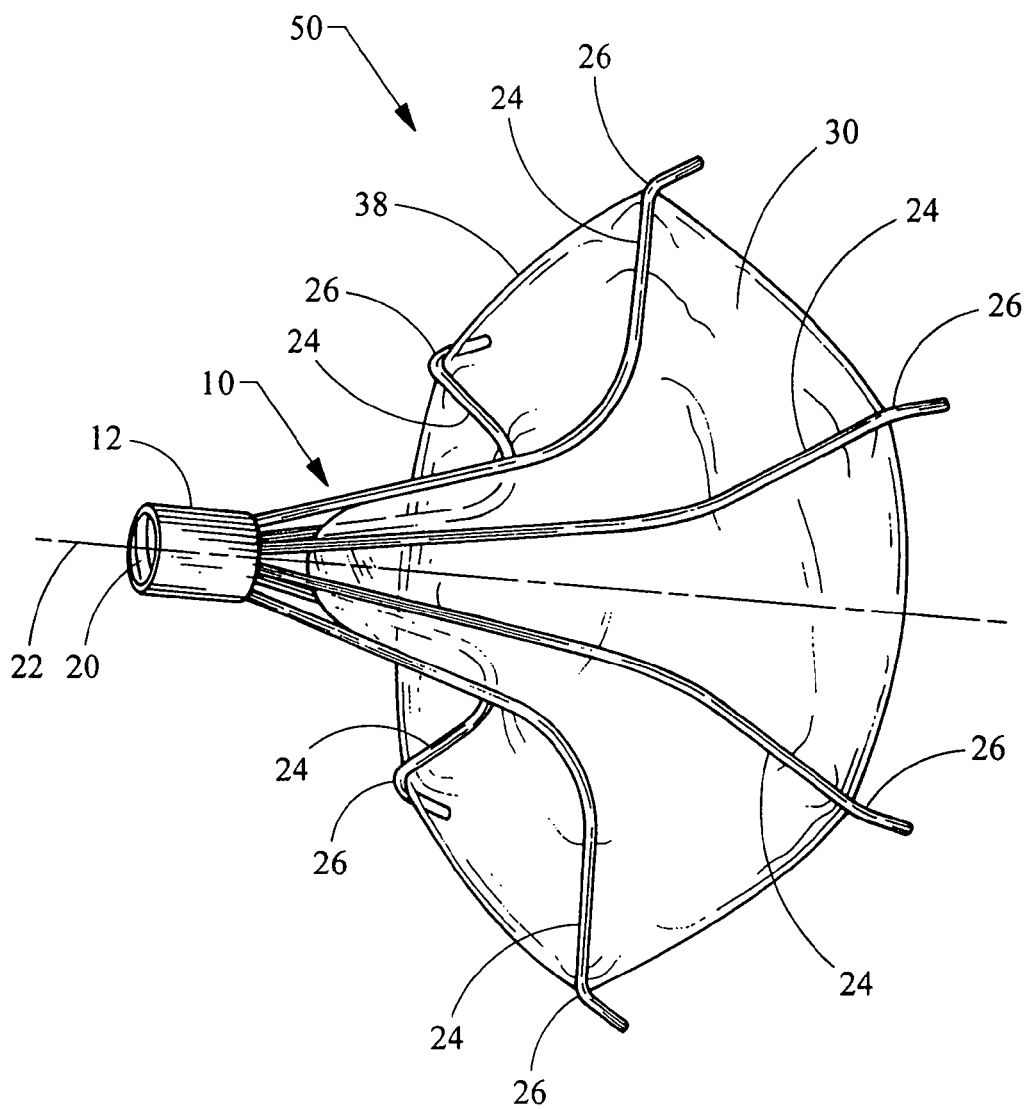
FIG. 2 is a perspective view of one embodiment of a completed occlusion device.

Referring now to FIG. 1, an apparatus 8 for making an occlusion device for occluding a body cavity is shown. As its primary components, the apparatus 8 includes a frame 10 having a plurality of arcuate legs 24 and a mandrel 32 having a base layer 38 made of a biocompatible material. The base layer 38 is disposed between an outer surface 34 of the mandrel 32 the arcuate legs 24 of the frame 10. The occlusion device is formed by attaching the arcuate legs 24 to the base layer 38 to form a membrane 30 extending along and between each of the arcuate legs as best shown in FIG. 2.

The frame 10 includes a hub 12 extending along a longitudinal axis 22 from a proximal end 14 to a distal end 16. The frame 10 optionally has a tubular wall 18 defining a lumen 20. A plurality of arcuate legs 24 are attached to the first hub 12 and extend distally to a distal leg portion 26. The plurality of arcuate legs 24 are flexible and have inner surfaces 28 defining an inner profile. Preferably, the arcuate legs 24 are attached to the distal end 16 of the hub 12. The arcuate legs 24, and hence the inner surfaces 28 defining the inner profile, extend radially away from the longitudinal axis 22 when in an unconstrained state. While the exact number of the first plurality of legs 24 may vary depending on the needs of a particular application, the present example illustrates six legs. In other examples, the distal portion 26 of the legs may further include an angled distal end segment 27 to, for example, anchor the occlusion device to a body vessel (not shown). The distal end segment 27 may, for example, be angled back toward the longitudinal axis 22.

At least part of the frame 10 may be made of any suitable material such as a superelastic material, stainless steel wire, cobalt-chromium-nickel-molybdenum-iron alloy, or cobalt-chrome alloy. It is understood that the frame 10 may be formed of any suitable material that will result in a self-opening or self-expanding frame 10, such as shape memory material. Shape memory materials or alloys have the desirable property of becoming rigid, i.e., returning to a remembered state, when heated above a transition temperature. A shape memory material suitable for the present invention includes alloys of nickel-titanium (Ni—Ti) available under the more commonly known name Nitinol. When this material is heated above the transition temperature, the material undergoes a phase transformation from martensite to austenite, such that material returns to its remembered state. The transition temperature is dependent on the relative proportions of the alloying elements Ni and Ti and the optional inclusion of alloying additives.

In one embodiment, the frame 10 is made from Nitinol with a transition temperature that is slightly below normal body temperature of humans, which is about 98.6° F. Thus, when the frame 10 is deployed in a body vessel and exposed to normal body temperature, the alloy of the frame 10 will transform to austenite, that is, the remembered state, which for one embodiment of the present invention is the expanded state when the frame 10 is deployed in the body vessel. To remove the frame 10 it is cooled to transform the material to martensite which is more ductile than austenite, making the frame 10 more malleable. As such, the frame 10 can be more easily collapsed and pulled into a lumen of a catheter for removal.

In another embodiment, the frame 10 is made from Nitinol with a transition temperature that is above normal body temperature of humans, which is about 98.6° F. Thus, when the frame 10 is deployed in a body vessel and exposed to normal body temperature, the frame 10 is in the martensitic state so that the frame 10 is sufficiently ductile to bend or form into a desired shape, which for the present invention is the expanded state. To remove the frame 10, the frame 10 is heated to transform the alloy to austenite so that it becomes rigid and returns to a remembered state, which for the frame 10 is a collapsed state.

As shown in FIG. 1, the mandrel 32 is configured to have the biocompatible material be releasably disposed onto the outer surface 34 between the frame 10 and the mandrel 32 to form the base layer 38. In one embodiment, a shape of the outer surface 34 is preferably configured to be slightly smaller than the inner profile defined by the inner surfaces 28 of the arcuate legs 24 to account for a thickness of the base layer 38. This allows a shape of the base layer 38 to correspond to the inner profile of the arcuate legs 24.

In one example, the mandrel 32 may be formed from, or coated with, an inert material (e.g., glass or stainless steel) to facilitate manufacturing the base layer 38. The mandrel may be cleaned with isopropyl alcohol prior to use and the outer surface 34 may then be immersed in a liquid solution of the biocompatible material, or alternatively, may be sprayed with the liquid solution of the material. The concentration of liquid solution of the material may be fine tuned to provide the desired viscosity. The viscosity of the solution may not only influence the rate of application, by dipping or spraying, but may also affect the thickness of the base layer 38. The thickness of the layer may also be increased by dipping or spraying the mandrel repeatedly, until the desired thickness is achieved. Once a desired thickness is achieved, the base layer 38 is allowed to cure into a solid. When the base layer 38 cures, it will have the shape of the outer surface 34.

FIG. 2 shows one example of a vascular occlusion device 50 made using the apparatus 8. As noted above, the biocompatible material is attached to and extends distally along and between the length of each of the first plurality of legs 24, approximately from the first hub 12 to the distal portion 26 of the legs 24. In this example, it forms the membrane 30 along and between each of the legs 24. The membrane 30 provides the structure to occlude a body vessel (not shown) when the occlusion device 46 is deployed in the body vessel.

Figure 3:
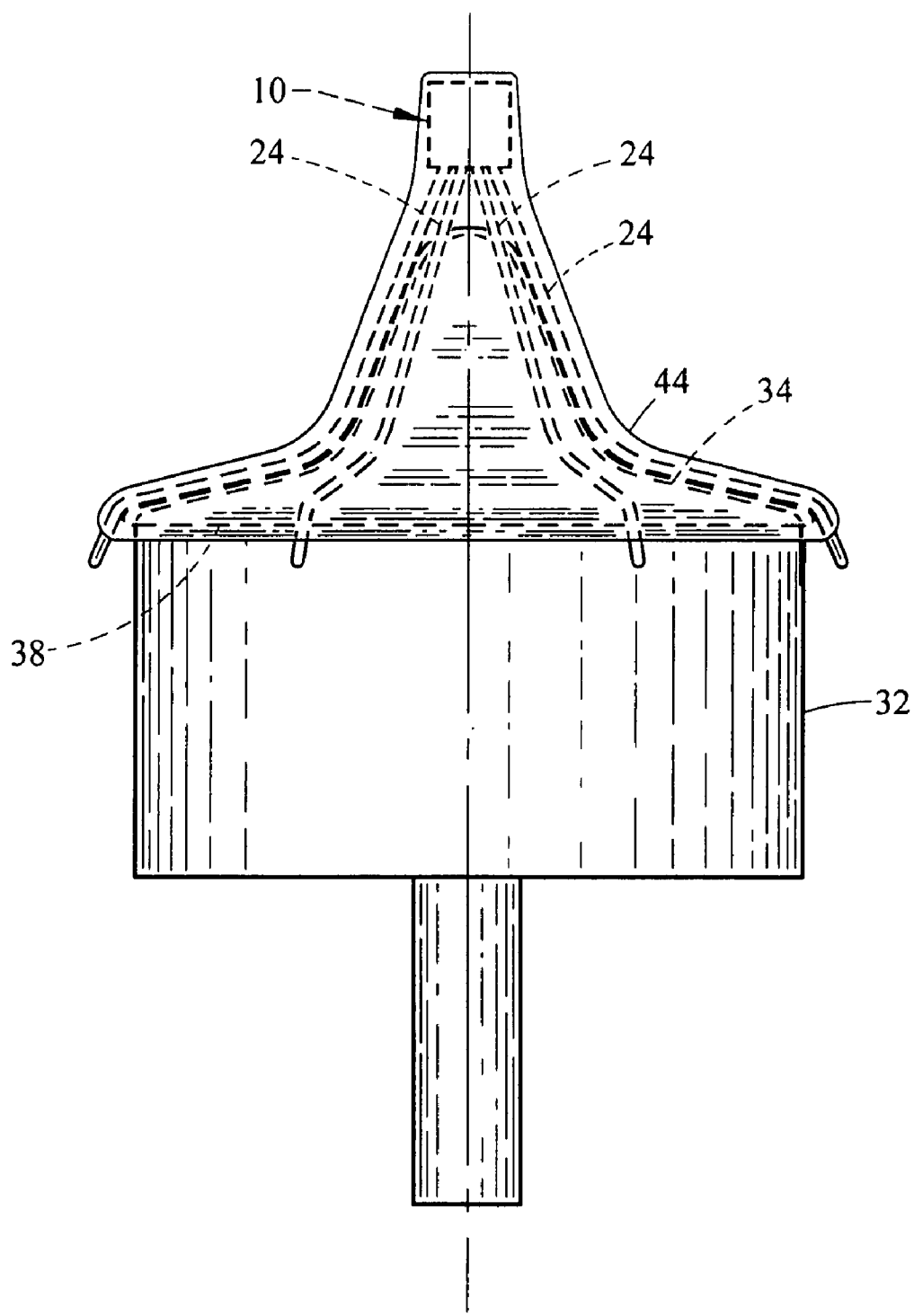
FIG. 3 is a side view of another embodiment of the apparatus of FIG. 1 having a second layer of the biocompatible material disposed thereon.
Figure 4:
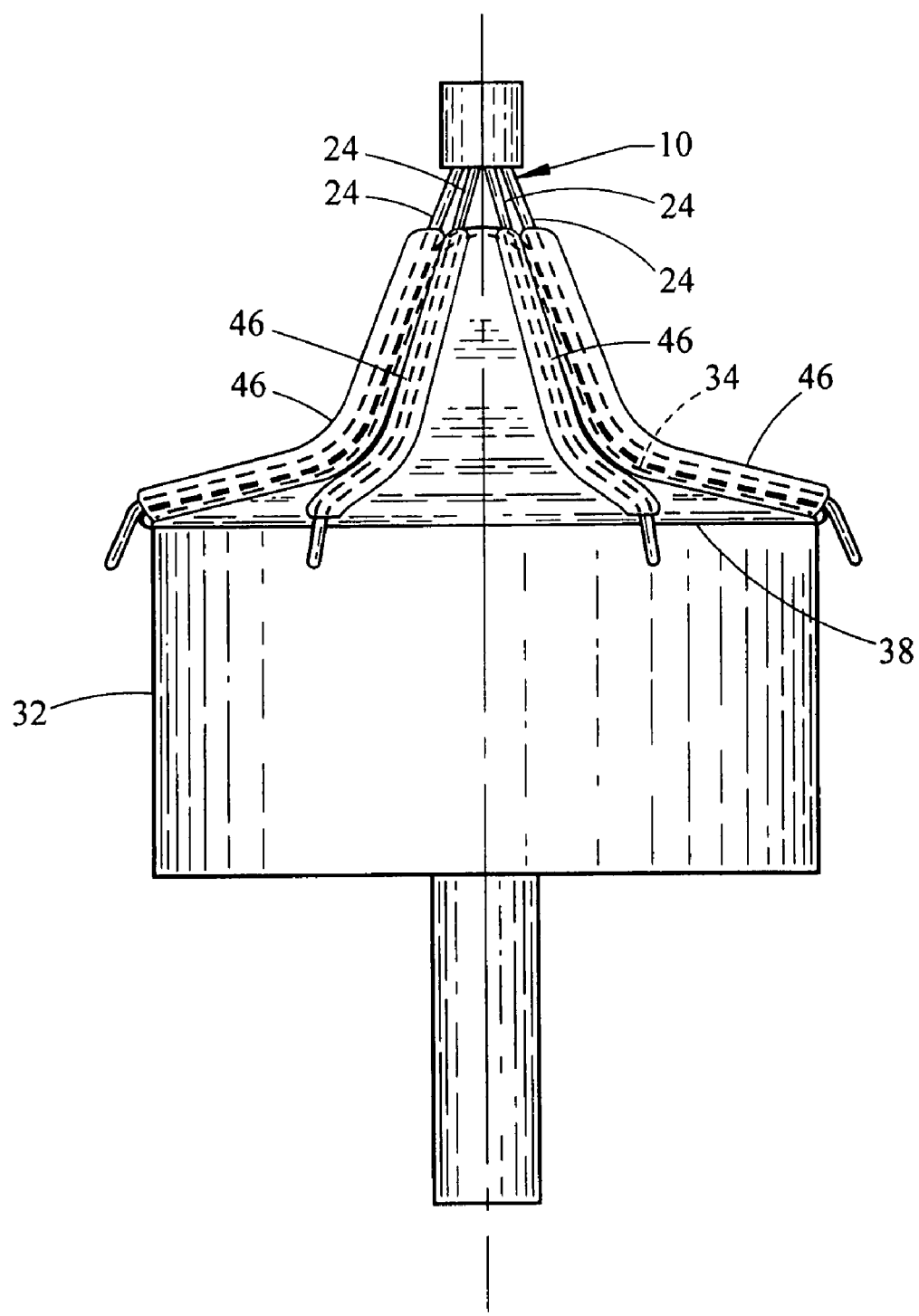
FIG. 4 is a side view of a third embodiment of the apparatus of FIG. 1.
Figure 5:
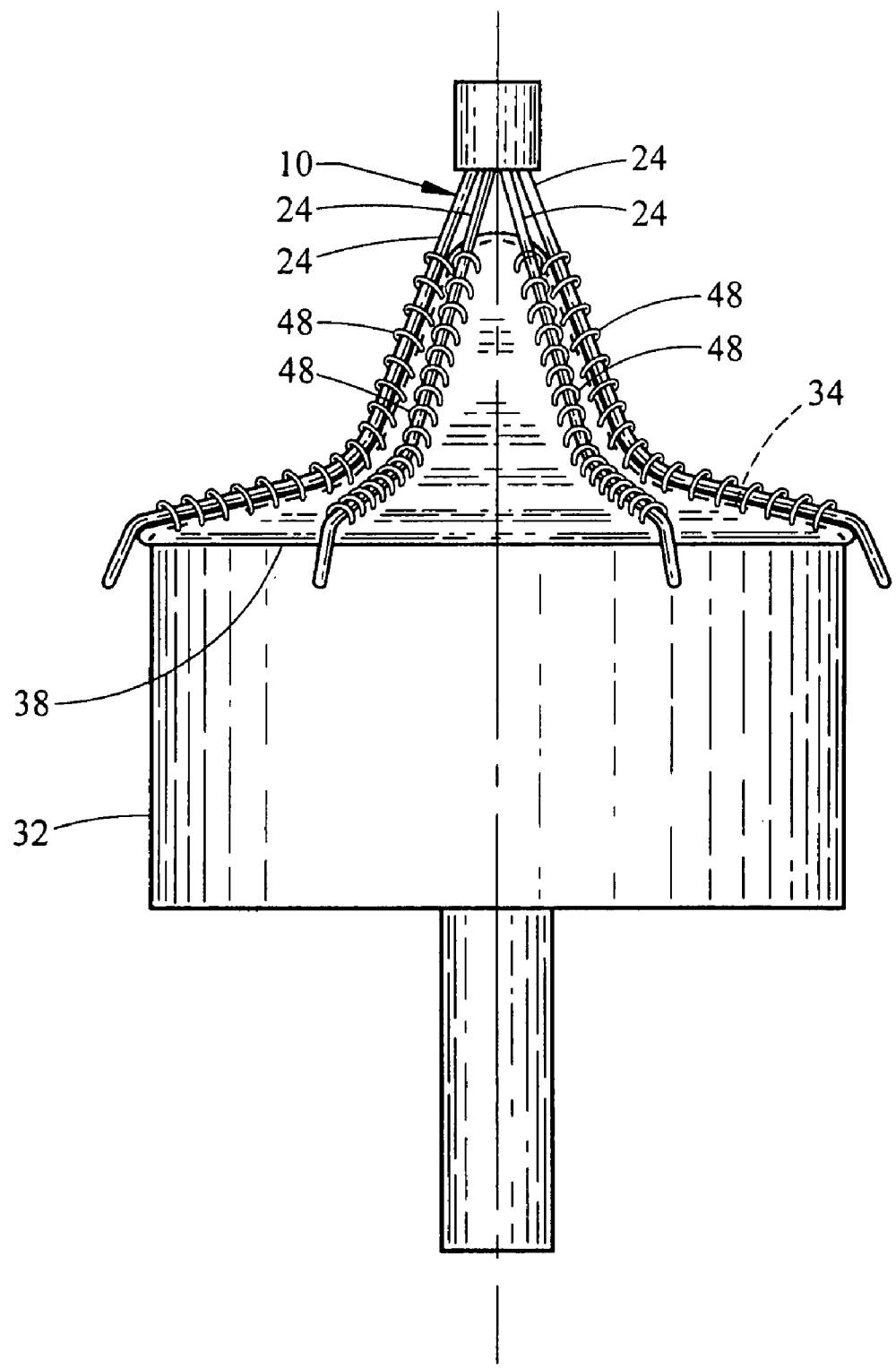
FIG. 5 is a side view of a fourth embodiment of the apparatus of FIG. 1.

Turning now to FIG. 3, a second layer 44 of additional biocompatible material is disposed over at least a portion of the frame 10. The second layer 44 is attached to the base layer 38 and encapsulates the arcuate legs 24 to attach them to the base layer 38. In this example, the entire frame 10 is covered and substantially encapsulated by the second layer 44. In another example, best shown in FIG. 4, a plurality of second layers 46 are locally disposed over a portion of each of the arcuate legs 24 and attached to the base layer 38. In this example, only the local portion of the arcuate legs 24 of the frame 10 are encapsulated by the second layers 46. In still another example shown in FIG. 5, a portion of each of the arcuate legs 24 may be attached to the base layer 38 by stitching. In the example shown, threads 48 may be used to stitch through the base layer 38 and over the arcuate legs 24 to attach the base layer 38 to the arcuate legs 24.

The biocompatible material includes any suitable material configured to prevent blood, emboli and other fluids from passing through the body vessel. In one embodiment, the biocompatible material may be made of nylon, rayon, silicone, polyester, biocompatible polyurethanes, polytetrafluoroethylene (known as PTFE or under the trade name Teflon™), urethane, and mixtures thereof without falling beyond the scope or spirit of the present invention. In one example, the material may be made of one material and coated with another, such as the biocompatible polyurethane. In another example, the material may be made from the biocompatible polyurethane.

One example of the biocompatible polyurethane is sold under the trade name THORALON (THORATEC, Pleasanton, Calif.). Descriptions of suitable biocompatible polyureaurethanes are described in U.S. Pat. Application Publication No. 2002/0065552 A1 and U.S. Pat. No. 4,675,361, both of which are herein incorporated by reference. Briefly, these publications describe a polyurethane base polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be manipulated to provide either porous or non-porous THORALON. The present invention envisions the use of non-porous THORALON. Non-porous THORALON can be formed by mixing the polyetherurethane urea (BPS-215) and the surface modifying additive (SMA-300) in a solvent, such as dimethyl formamide (DMF), tetrahydrofuran (THF), dimethyacetamide (DMAC), dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandrel or a mold. In one example, the composition can be dried to remove the solvent.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

A variety of other biocompatible polyurethanes/polycarbamates and urea linkages (hereinafter "—C(O)N or CON type polymers") may also be employed. These include CON type polymers that preferably include a soft segment and a hard segment. The segments can be combined as copolymers or as blends. For example, CON type polymers with soft segments such as PTMO, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

Preferably, the hard segment is formed from a diisocyanate and diamine. The diisocyanate may be represented by the formula OCN-R-NCO, where —R— may be aliphatic, aromatic, cycloaliphatic or a mixture of aliphatic and aromatic moieties. Examples of diisocyanates include MDI, tetramethylene diisocyanate, hexamethylene diisocyanate, trimethylhexamethylene diisocyanate, tetramethylxylylene diisocyanate, 4,4'-dicyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3'-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methylpentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, 1,6-hexanediol, 1,8-octanediol, propylene glycols, 2,3-butylene glycol, dipropylene glycol, dibutylene glycol, glycerol, or mixtures thereof.

Biocompatible CON type polymers modified with cationic, anionic and aliphatic side chains may also be used. See, for example, U.S. Pat. No. 5,017,664. Other biocompatible CON type polymers include: segmented polyurethanes, such as BIOSPAN; polycarbonate urethanes, such as BIONATE; and polyetherurethanes, such as ELASTHANE; (all available from POLYMER TECHNOLOGY GROUP, Berkeley, Calif.).

Other biocompatible CON type polymers can include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Pat. Application Publication No. 2002/0187288 A1, which is incorporated herein by reference.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589 which is incorporated herein by reference.

Another instance of a vascular occlusion device (not shown) includes a plurality of small holes (not shown) in the membrane 30 (see FIG. 2). While the small holes may be formed using any appropriate means, one preferred method includes, but is not limited to, laser cutting. Using an automated laser cutting device (not shown) any appropriate pattern and size of small holes 40 may be cut into the membrane 30. Laser cutting has the advantage that it may be accomplished while the occlusion device is on or off of the mandrel 32 (see FIG. 1). When the small holes are cut on the mandrel 32, lasers have the further advantage that their power may be adjusted to be high enough to cut the biologically compatible material but low enough to leave the mandrel 32 unharmed. The small holes may be large enough to allow blood to pass but small enough to stop emboli. Alternatively, the small holes may only be large enough to permit a small amount of blood to weep through the membrane 30 to improve adherence of clotting blood to the membrane to occlude a body vessel. The holes should be sized to allow only a small amount of blood to weep through and coat both sides of the membrane 30. As a result, the blood will clot on both sides, as well as within the holes 40, of the membrane 30. One example of an appropriate diameter of the holes includes, but is not limited to, 0.001 inch.

Figure 6:
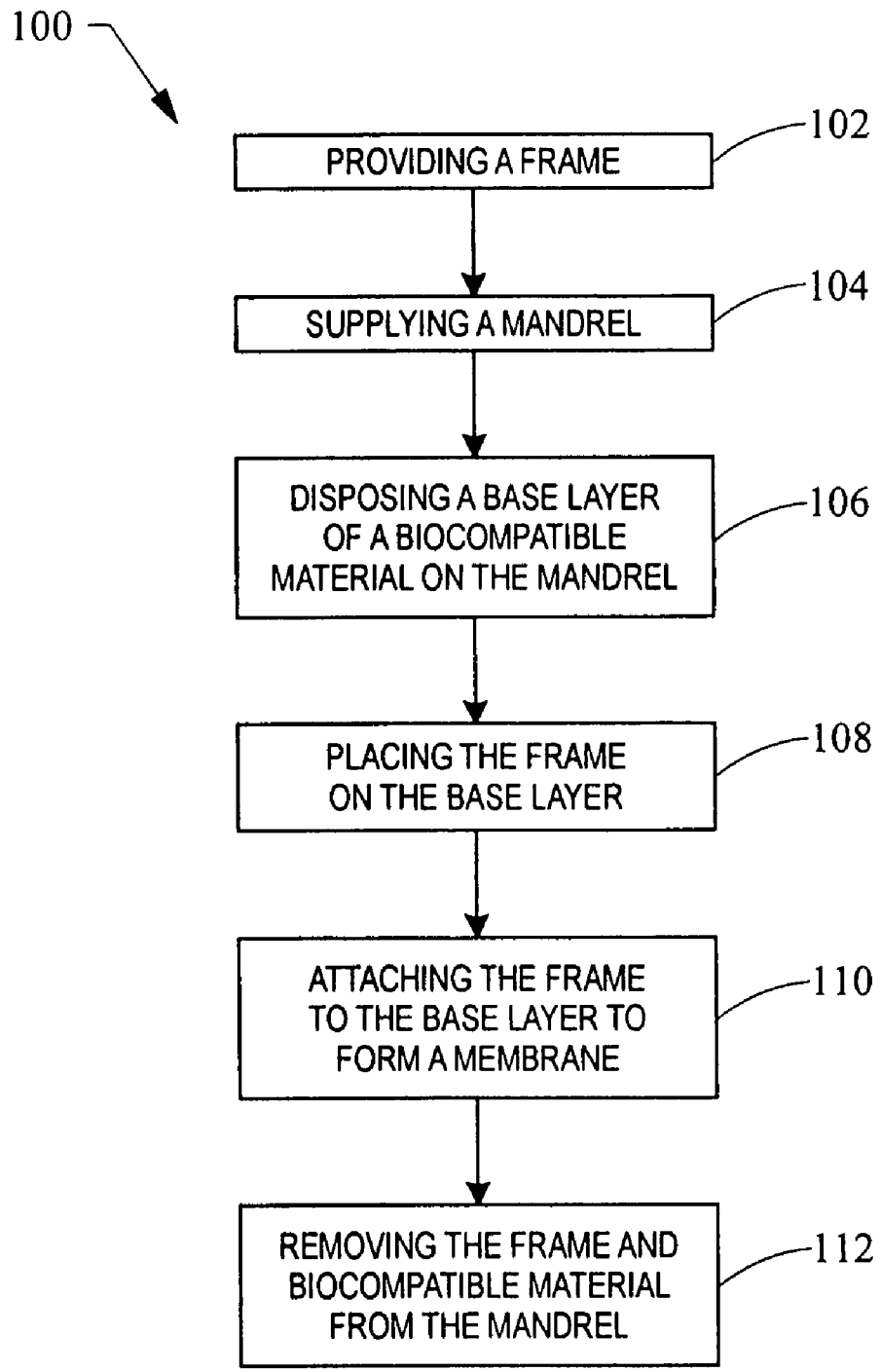
FIG. 6 is a flow-chart describing a method of making an occlusion device according to the present invention.

Turning to FIG. 6, a flow chart designated at 100 is provided describing a method for making an occlusion device for occluding a body vessel such as a blood vessel. The method includes providing any of the frames and mandrels described herein at boxes 102 and 104 respectively. Box 106 includes disposing a base layer of biocompatible material on an outer surface of the mandrel and box 108 places the frame on the base layer on the mandrel such that at least part of the frame contacts the base layer. Box 110 attaches the frame to the base layer such that the biocompatible material forms a membrane extending along and between arcuate legs of the frame, and box 112 removes the frame and biocompatible material from the mandrel to form the finished occlusion device.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

We claim:

1. An apparatus for making a vascular occlusion device for occluding a body cavity, the apparatus comprising:
    a frame including a hub extending along a longitudinal axis from a proximal end to a distal end, a plurality of arcuate legs being attached to the hub and extending distally to a distal leg portion, the arcuate legs being flexible and having inner surfaces defining an inner profile extending radially away from the longitudinal axis in an unconstrained state;
    a mandrel having an outer surface and a biocompatible material being releasably disposed thereon, the outer surface corresponding to the inner profile of the arcuate legs; and
    the inner surfaces of the arcuate legs of the frame being disposed over the outer surface of the mandrel onto the base layer and at least the arcuate legs being attached to the base layer to form a membrane extending along and between each of the arcuate legs.

2. The apparatus of claim 1 wherein the biocompatible material is disposed on the outer surface of the mandrel as a liquid material and is allowed to cure into a solid to form the base layer.

3. The apparatus of claim 1 wherein additional biocompatible material is disposed over at least a portion of the frame and attached to the base layer to encapsulate and attach at least part of the arcuate legs to the base layer.

4. The apparatus of claim 1 wherein the arcuate legs are attached to the base layer by stitching a portion of the base layer to each of the arcuate legs.

5. The apparatus of claim 1 further comprising a laser cutting means being configured to cut a plurality of small holes in the membrane.

6. The apparatus of claim 1 wherein the frame is made of a shape memory material.

7. The apparatus of claim 3 wherein the shape memory material includes alloys of nickel-titanium.

8. The apparatus of claim 1 wherein the biocompatible material includes at least one of nylon, rayon, silicone, polyester, polytetrfluroethylene, urethane, biocompatible polyurethanes, and mixtures thereof.

* * * * *